United States Patent [19]

Brunke et al.

[11] Patent Number: 5,294,602
[45] Date of Patent: Mar. 15, 1994

[54] 3-(HEXENYLOXY)-PROPANE-NITRILE, ITS PRODUCTION AND USE

[76] Inventors: Ernst-Joachim Brunke, Pippingsbusch 3, 3450 Holzminden; Karl-Georg Fahlbusch, Allenbergstr. 40, 3470 Hoexter 1, both of Fed. Rep. of Germany

[21] Appl. No.: 795,108

[22] Filed: Nov. 20, 1991

[30] Foreign Application Priority Data

Nov. 20, 1990 [DE] Fed. Rep. of Germany ....... 4037345

[51] Int. Cl.$^5$ ...................... A61K 7/46; C07C 255/13
[52] U.S. Cl. ....................................... 512/6; 558/449; 558/450; 558/447
[58] Field of Search ....................... 558/447, 449, 450; 512/6

[56] References Cited

U.S. PATENT DOCUMENTS

| 2,280,790 | 4/1942 | Bruson | 558/449 |
|---|---|---|---|
| 2,445,652 | 7/1948 | Whetstone | 558/447 |
| 4,115,326 | 9/1978 | Plattier et al. | 558/449 X |
| 4,709,072 | 11/1987 | Merger et al. | 558/447 X |

FOREIGN PATENT DOCUMENTS 2601825 7/1977 Fed. Rep. of Germany ...... 558/447

OTHER PUBLICATIONS

"Organic Reactions", vol. V, Cyanoethylation Chapter by Bruson, pp. 89-93 and 121-127, (1949).

*Primary Examiner*—Joseph Paul Brust

[57] ABSTRACT

The 3-(hexenyloxy)-propane-nitriles of general formula A, in which $R^1$ and $R^2$ are optionally a hydrogen atom or a methyl group and $R^3$ is an unbranched hexenyl group, are new and are useful as odour materials such as ingredients for perfume compositions. Their production is carried out through the base catalysed addition of acrylonitrile or methyl substituted acrylonitrile to the unbranched hexenol, in which the reaction temperature is between 0° and 50° C. (for acrylonitrile especially between 0° and 10° C., for crotonitrile especially between 15° and 25° C. and for methacrylonitrile, especially between 30° and 40° C.), and the aforesaid base is benzyl trimethylammonium hydroxide (Triton B).

2 Claims, No Drawings

3-(HEXENYLOXY)-PROPANE-NITRILE, ITS PRODUCTION AND USE

The object of the invention is new 3-(hexenyloxy)-propane-nitriles of the general formula A $$R^3—O—CHR^1—CHR^2—CN \qquad A$$

in which $R^3$ is an unbranched hexenyl residue and $R^1$ and $R^2$ are optionally a hydrogen atom or a methyl group. The production of the new oxypropane nitriles results from a manner which is known itself through the addition of alpha, beta unsaturated nitriles to corresponding hexenol in the presence of a base as catalyst. The new compounds of formula A have unusual odour properties and can thereby be used as fragrances or constituents of perfume oils.

In the perfume industry there is a constant demand for new original olfactory skin compatible and stable compounds. These requirements are partly filled by various classes of substances. Of industrial significance are several aliphatic nitriles which have been shown to have good stability. Amongst these are geranylnitrile, citronellylnitrile and tridecen-2-nitrile, which have at their disposal citrus-like perfume notes of high intensity and stability of that type of nitrile. It is also true that they provide fatty and metallic notes, which limits their use for inclusion in perfume oils. The reported perfume properties of oxypropane nitriles (also known as beta oxynitriles) is relatively scarce, in the literature, amongst them being the following:

a) German Offenlegungsschrift 2639182 describes the compound 3-(10-undecenyloxy)propion-nitrile as a compound with a weak fruity aroma and a salicylate type note with powdery characteristics.

b) German Offenlegungsschrift 2601825 describes oxy-propane-nitriles, prepared from acrylonitrile and on the one hand saturated fatty alcohol and on the other hand a terpene alcohol, thereby the resulting ethernitriles have an aroma reminiscent of the starting alcohol.

c) In the Journal "Perfumes, Aromas, Cosmetics" 1975, S.34 is described the synthesis and perfume properties of known beta oxynitriles. Acrylonitrile is here added to saturated aliphatic alcohols, terpene alcohols and cyclic and aromatic alcohols. The perfume properties arise from the starting beta-oxynitrile.

In the hitherto known 3-oxynitriles or nitriles there are no known compounds with natural leafy green notes. It is thus new and unexpected that the here described compounds of Formula A result in naturally acting green notes, which in part are reminiscent of violet-leafed fragrance.

For the addition reaction of acrylonitrile to alcohols, various basic catalysts can be use ("Organic Reactions", V, 1952,S89 Cyanoethylation, and literature cited therein). Thus the reaction proceeds with sodium, sodium methanolate, sodium hydroxide or with a quaternary ammonium based Triton B (benzyltrimethylammonium hydroxide) at temperatures of 10° to 50° C. in good yield. The new compounds of formula A, set out as the compounds 1 to 9, can be prepared by the analogous reaction of acrylonitrile or methyl substituted acrylonitriles with non-branched acrylonitriles with unbranched hexenols.

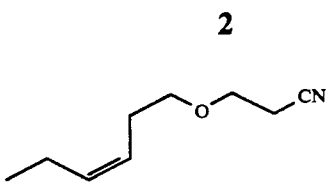
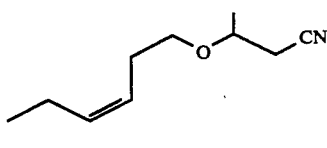
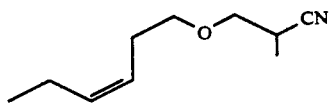
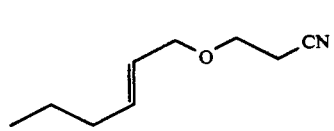
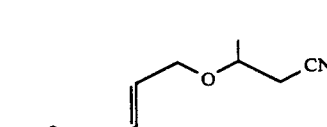
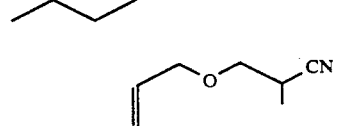
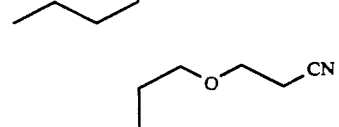
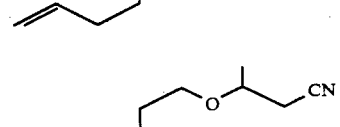
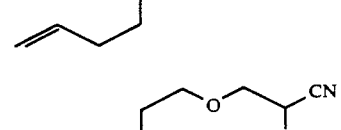

The new compounds of formula A display remarkable perfume properties, which collectively go in the natural green odour direction and are characterised by considerable perfume strength. The perfume characteristics of the oxynitriles A are clearly different from those of the respective starting alcohols. In addition to the strong green notes, especially the 3-(cis-hex-3-enyloxy)-propane-nitrile (1) has also fruity and flowery aspects with a strong radiation in the head notes. Surprisingly, the compounds of formula A, which in contrast to the starting alcohol are stable both in basic and acidic regions, have a substantially stronger adhesiveness to fibres than the starting alcohols.

The physico-chemical properties and the strong fresh green aroma notes are valuable properties for perfumery. The compounds of formula A are especially good for improving, strengthening, or modifying the characteristics of perfume oils. The following examples are to illustrate the invention without limiting the scope thereof.

EXAMPLE 1

Preparation of the Alkenyl-Oxypropane Nitriles

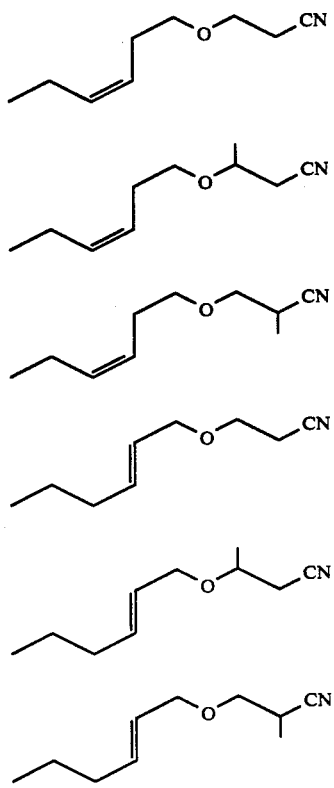

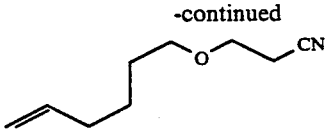

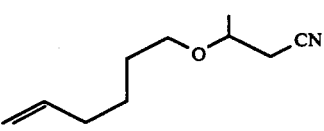

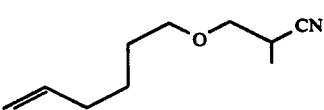

In a 500 ml stirring apparatus (reflux condenser, thermometer, stirring motor, dropping funnel) were charged 1 mole of unsaturated unbranched alcohol and 0.01 mole of the phase transfer catalyst Triton B. To this was added dropwise after four to six hours, 1.1 to 1.2 moles of unsaturated nitrile at the following temperatures: 0° to 10° C. for acrylonitrile; 15° to 20° C. for crotonitrile; 30° to 40° C. for methacrylonitrile. After about fifteen hours stirring at room temperature was then added to the same mix diethylether, then 100 ml water and 5 to 10 ml 10% sulphuric acid. The mixture was then intensively shaken. The organic phase was washed with concentrated hydrochloric acid, dried under reduced pressure. The crude product was then distilled over a 20 cm glass body-filled column. The product obtained had the properties shown in Table 1.

TABLE 1

Physical Characteristics and Yields of Compounds 1 to 9, as well as their Perfume Characteristics.

| Nr | $R^3$—O—$CHR^1$—$CHR^2$—CH | $n_D^{20}$ | $D_4^{20}$ | Boiling Point [°C./mm] | Yield [%] | Perfume Description |
|---|---|---|---|---|---|---|
| 1 | $R^1$ = H<br>$R^2$ = H<br>$R^3$ = cis-3-hexenyl | 1.4456 | 0.9074 | 86/2 | 80 | Strong, green and fruity, flowery (violet leaves). |
| 2 | $R^1$ = CH3<br>$R^2$ = H<br>$R^3$ = cis-3-hexenyl | 1.4439 | 0.8930 | 93/3 | 72 | Strong, green, flowery, aldehyde-like; somewhat like cucumber. |
| 3 | $R^1$ = H<br>$R^2$ = CH3<br>$R^3$ = cis-3-hexenyl | 1.4413 | 0.8875 | 100/2.5 | 66 | Green, flowery, fruity (bananas, melons). |
| 4 | $R^1$ = H<br>$R^2$ = H<br>$R^3$ = trans-2-hexenyl | 1.4441 | 0.9014 | 93/1 | 87 | Strong, sweet, fruity (pears, apples), Cabbage-like flowery. |
| 5 | $R^1$ = CH3<br>$R^2$ = H<br>$R^3$ = trans-2-hexenyl | 1.4434 | 0.8917 | 98/0.6 | 76 | Green, somewhat cabbage-like chemical. |
| 6 | $R^1$ = H<br>$R^2$ = CH3<br>$R^3$ = trans-2-hexenyl | 1.4406 | 0.8860 | 49/0.5 | 56 | Green, fungal somewhat metallic. |
| 7 | $R^1$ = H<br>$R^2$ = H<br>$R^3$ = 5-hexenyl | 1.4404 | 0.9011 | 96/3 | 77 | Strong, green, fruity (apple) aldehyde-like. |
| 8 | $R^1$ = CH3<br>$R^2$ = H<br>$R^3$ = 5-hexenyl | 1.4404 | 0.8901 | 70/0.5 | 55 | Green, somewhat metallic. |
| 9 | $R^1$ = H<br>$R^2$ = CH3<br>$R^3$ = 5-hexenyl | 1.4376 | 0.8844 | 65/0.5 | 58 | Strong, green, fruity somewhat sweet. |

EXAMPLE 2

Spectroscopic Data of
3-(cis-hex-3-enyl-oxy)-propane-nitrile(1)

Empirical formula $C_9H_{15}NO$ (153.23)

IR (Film): 2254 (CN), 1654 (C=C), 1113 (C—O—C) cm$^{-1}$.

$^1$H-NMR (CDCl$_3$, 300 MHz): δ=5.47 (m, 1H, H-olefin.), 5.35 (m, 1H) H-olefin.), 3.66 (t, J=6.5 Hz; 2H, CH$_2$), 3,49 (t 2.34 (q, J=7.7 Hz; 2H, CH$_2$), 2.06 (p, J=6.1 Hz; 2H, CH$_2$), 0.97 (t, J=7.6 Hz; 3H, CH$_3$).

$^{13}$C-NMR (CDCl$_3$, 75 MHz): δ=134.0 (C-olefin.; d), 124.4 (C-olefin.; d), 117.8 (CN; s), 71.1 (C-1'; t), 65.4 (C-3; t), 27.7 (C-2; t), 20.6 (C-2'; t), 18.9 (C-5'; t), 14.2 (C-6'; q).

MS: m/e=153 (2%, M+), 138 (2%), 124 (4%), 110 (7%) 91 (5%), 84 (19%), 82 (38%), 69 (19%), 67 (65%), 54 (100%), 41 (63%).

EXAMPLE 3

Spectroscopic Data of
3-(cis-hex-3-enyl-oxy)-butane-nitrile(2)

Empirical formula $C_{10}H_{17}NO$ (167.25)

IR (Film): 252 (CN), 1652 (C=C), 1104 (C—O—C) cm$^{-1}$.

$^1$H-NMR (CDCl$_3$, 300 MHz): δ=5.45 (m; 1H, H-olefin.), 5.35 (m; 1H, H-olefin.), 3.72 (sex.; J=6.1 Hz; 2H, CH$_2$), 3,47(m, 2H, CH$_2$), 2.50 (d; J=5.7 Hz; 2H, CH$_2$), 2.31 (q, J=7.7 Hz; 2H, CH$_2$), 2.06 (p, J=7.7 Hz; 2H, CH$_2$), 1.29 (d; J=6.1 Hz; 3H, CH$_3$), 0.96 (t, J=7.5 Hz; 3H, CH$_3$).

$^{13}$C-NMR (CDCl$_3$, 75 MHz): δ=133.8 (C-olefin.; d), 124.7 (C-olefin.; d), 117.5 (CN; s), 71.2 (C-1'; t), 68.9 (C-3; d), 28.0 (C-2; t), 25.0 (C-2'; t), 20.7 (C-5'; t), 19.7 (C-4; q), 14.2 (C-6'; q).

MS: m/e=167 (1%, M+), 152 (1%), 138 (1%), 124 (2%), 111 (2%), 98 (10%), 82 (40%), 68 (100%), 67 (37%), 55 (12%), 41 (15%).

EXAMPLE 4

Spectroscopic Data of
3-(cis-hex-3-enyl-oxy)-2-methyl-propane-nitrile(3)

Empirical formula $C_{10}H_{17}NO$ (167.25)

IR (Film): 2245 (CN), 1653 (C=C), 1120 (C—O—C) cm$^{-1}$.

$^1$H-NMR (CDCl$_3$, 300 MHz): δ=5.45 (m, 1H, H-olefin.), 5.35 (m, 1H, H-olefin.), 3.49 (t, J=6.9 Hz; 2H, CH$_2$), 3.49-3.57 (m; 2H, CH$_2$), 2.85 (sec., J=6.1 Hz; 1H, CH); 2.33 (q, J=7.0 Hz; 2H, CH$_2$), 2.06 (p, J=6.1 Hz; 2H, CH$_2$), 1.32 (d, J=7.1 Hz; 3H, CH$_3$), 0.97 (t, J=7.5 Hz; 3H, CH$_3$).

$^{13}$C-NMR (CDCl$_3$, 75 MHz): δ=133.9 (C-olefin.; d), 124.6 (C-olefin.; d), 121.4 (CN; s), 71.5 (C'-1; t), 71.2 (C-3; t); 27.7 (C-2'; t), 26.6 (C-2; d), 20.7 (C-5=; t); 14.7 (CH$_3$; q), 14.2 (C-6', q).

MS: m/e=167 (1%, M+), 152 (1%), 138 (2%), 124 (5%), 111 (2%), 98 (17%), 82 (54%), 68 (100%), 67 (63%), 54 (16%), 41 (19%).

EXAMPLE 5

Stability Test with Compound 1

Compound 1 was compounded in commercial base for perfume oil in commercial doses. The odour assessment was carried out one day after compounding, after one month or three months storage at room temperature, and 40° C. The assessment "very good" (VG) indicates that no odour like variables were detected. The assessment "good" (G) indicates a slight but still acceptable modification of the odour, while the assessment "not good" (NG) indicates a clear modification of the odour. For the odour assessment, it was compared with a standard sample stored at 18° C. (in the same base).

The irradiation with synthetic daylight led to trivial discolouration with while soap, which is comparable to the same with amyl cinnamaldehyde or methyl ionone, with the same base and dose.

| Base | Dosage | Standard | 1 Month Room Temp | 1 Month 40° C. | 3 Month Room Temp | 3 Month 40° C. |
| --- | --- | --- | --- | --- | --- | --- |
| Acid Cleanser (pH 1,8) (H$_3$PO$_4$) | 0,2 | VG | VG | VG | VG | G |
| Acid Cleanser (pH 1,8) (HCHOOH) | 0,3 | VG | VG | G | G | G |
| Alkali Cleanser (pH 10,5) | 0,4 | VG | VG | G | VG | G |
| White Soap | 1,0 | VG | VG | VG | G | G |
| Washing Agent without EDTA | 0,2 | VG | G | G | G | G |
| Washing agent with EDTA | 0,2 | VG | VG | G | VG | G |
| Soft Rinsing Agent | 0,2 | VG | VG | VG | VG | G |
| Foam Bath | 1,5 | VG | VG | VG | VG | G |
| Shampoo | 0,5 | VG | G | G | G | G |
| Aerosol/Antiperspirant | 0,4 | VG | G | G | G | G |
| Deo-Spray | 0,3 | VG | VG | VG | G | G |
| Day Cream o/e Emulsion | 0,3 | VG | G | G | G | G (−) |
| Cream w/o Emulsion | 0,3 | VG | G | G (−) | G | G (−) |

EXAMPLE 6

Perfume Composition—Green-Woody Type

| | A | B |
| --- | --- | --- |
| 3-(cis-Hex-3'-enyl-oxy)-propane-nitrile(1) | — | 1 |
| Bergamot Oil | 10 | 10 |
| Wormwood Oil | 1,5 | 1,5 |
| Dihydromyrcenol | 5 | 5 |

-continued

|  | A | B |
| --- | --- | --- |
| Lavender Oil | 2 | 2 |
| Beta-Ionone | 1 | 1 |
| Timberol$^R$ (DRAGOCO) | 10 | 10 |
| Iso-E-Super$^R$ (IFF) | 15 | 15 |
| Patchouli Oil | 3 | 3 |
| Lignofix$^R$ (Acetylcedrene, DRAGOCO) | 10 | 10 |
| Hedione$^R$ (Firmenich) | 5 | 5 |
| Galoxolide$^R$ 50 (IFF) | 18 | 18 |
| Lyral$^R$ (IFF) | 8 | 8 |
| Sandranol$^R$ (IFF) | 3 | 3 |
| Benzylsalicylate | 5 | 5 |
| Dipropylene glycol | 3,5 | 2,5 |
|  | 100,0 | 100,0 |

Mixture A had a calibrated odour of green-herbaceous Ambra-Notes with flowery and woody elements. In mixture B, the flowery element was unfolded and displayed through the strong green-flowery freshness of compound 1. The character of the headnotes was fortified by compound 1.

EXAMPLE 7

Perfume Composition—Flowery Type

|  | A | B |
| --- | --- | --- |
| 3-(cis-Hex-3'-enyl-oxy)-propane Nitrile(1) | — | 2,4 |

-continued

|  | A | B |
| --- | --- | --- |
| Benzyl-acetate | 7 | 7 |
| Di-(Methylbutyl)-carbinyl-acetate | 8,6 | 8,6 |
| Methyl-Ionone | 24 | 24 |
| Alpha Ionone | 6 | 6 |
| Hydroxinal extra (DRAGOCO) | 16 | 16 |
| Hedione$^R$ (Firmenich) | 10 | 10 |
| Isodamascone$^R$ (DRAGOCO) | 2 | 2 |
| Exaltolide$^R$ (Firmenich) | 8 | 8 |
| Benzylsalicylate | 16 | 16 |
| Dipropylene | 2,4 | — |
|  | 100,0 | 100,0 |

Mixture A had classic flowery elements. In mix B the addition of Compound 1 brought forward a strong green violet character. This shows the essential characteristics of the oxonitrile 1.

We claim:

1. A composition having an odor with leafy green notes comprising an amorphous mass uniformity mixed with an odor-producing amount of 3-(hexenyloxy)-propane-nitrile of the general formula $$R^3\text{—O—}CHR^1\text{—}CHR^2\text{—CN}$$

in which $R^3$ is an unbranched hexenyl residue and $R^1$ and $R^2$ are selected from the group consisting of H and $CH_3$.

2. The composition of claim 1 wherein said amorphous mass comprises perfume oil.

* * * * *